United States Patent [19]
Hoegnelid et al.

[11] Patent Number: 5,487,758
[45] Date of Patent: Jan. 30, 1996

[54] ELECTRODE SYSTEM FOR PACEMAKERS

[75] Inventors: Kurt Hoegnelid, Västerhaninge; Alf Oehman, Vaellingby, both of Sweden

[73] Assignee: Siemens-Elema AB, Solna, Sweden

[21] Appl. No.: 124,454

[22] Filed: Sep. 22, 1993

[30] Foreign Application Priority Data

Sep. 28, 1992 [SE] Sweden ................... 92027929

[51] Int. Cl.⁶ .................................................. A61N 1/05
[52] U.S. Cl. ........................................................ 607/123
[58] Field of Search ................................. 607/122, 119, 607/123, 127, 116

[56] References Cited

U.S. PATENT DOCUMENTS

| | | | |
|---|---|---|---|
| 3,416,533 | 12/1968 | Fisher et al. | 607/122 |
| 4,154,247 | 5/1979 | O'Neill . | |
| 4,317,458 | 3/1982 | Yokoyama | 607/122 |
| 4,463,765 | 8/1984 | Gold | 607/127 |
| 4,567,901 | 2/1986 | Harris . | |
| 4,624,266 | 11/1986 | Kane . | |
| 4,628,943 | 12/1986 | Miller . | |
| 4,932,407 | 6/1990 | Williams | 607/122 |
| 5,143,090 | 9/1992 | Dutcher et al. . | |

FOREIGN PATENT DOCUMENTS 020401  4/1991  WIPO .................... 607/127

*Primary Examiner*—William E. Kamm
*Assistant Examiner*—Scott M. Getzow
*Attorney, Agent, or Firm*—Hill, Steadman & Simpson

[57] ABSTRACT

An electrode system for pacemakers has at least one ventricular electrode, intended for placement in contact with heart tissue in the ventricle in order to sense electrical activity and stimulate and connected to a conductor for transmitting signals to and from the electrode. The part of the conductor nearest to the ventricular electrode is in the form of an insulated needle, helix or screw for puncturing or screwing into the part of the atrial wall facing the septum during implantation and having a sufficient length to permit the conductor to extend into the septum or superior part of the outer ventricular wall.

13 Claims, 3 Drawing Sheets

ELECTRODE SYSTEM FOR PACEMAKERS

BACKGROUND OF THE INVENTION

1. Field of the Invention

The present invention relates to an electrode system for pacemakers, of the type having at least one ventricular electrode, intended for placement in contact with heart tissue in the ventricle in order to sense electrical activity and stimulate and connected to a conductor for transmitting signals to and from the electrode.

2. Description of the Prior Art

Stimulation in both single chamber and dual chamber pacemakers with ventricular stimulation, i.e. VVI and DDD pacemakers, normally takes place in the apex. A conventional pacemaker of this type for treating patients suffering from e.g. bradycardia requires two additional electrodes, each with its own connecting conductor, one of these electrodes being placed in the heart's atrium and the other in the ventricle. The task of the electrodes is to sense electrical activity in the heart and to emit stimulation pulses when spontaneous electrical activity ceases.

One example of an electrode system of this type is described in e.g. U.S. Pat. No. 4,567,901. In this known system, the electrode cable is subdivided in a precurved area into an atrial section and a ventricular section, said sections in turn being curved so the atrial electrode and the ventricular electrode carried by them come to be disposed at the desired sites in the heart when the electrode system is implanted. Such an electrode system with a precurved electrode cable subdivided into two separate sections is a complex system which is difficult to implant in the patient.

There thus exists a need to achieve an Electrode system for DDD pacemakers with the electrode conductors bundled in a single cable.

In attempts to achieve such a simplification of the electrode system, electrode systems have been used previously with the conductors bundled in a single cable, at one end of which an ordinary stimulation and sensing electrode is arranged for implantation in the conventional manner in the ventricle near the apex. This type of electrode system also includes one or a plurality of electrodes arranged on the cable in the atrium of the heart. However, these atrial electrodes are "floating", i.e. they are normally not in direct contact with electrically active tissue, so effective stimulation is impossible, and sensing with the aid of these electrodes is more difficult.

In one attempt to bring the atrial electrode(s) into contact with the heart tissue in the atrium in order to stimulate there, the part of the cable carrying the atrial electrode(s) has been preshaped so the electrode(s) press(es) against the heart tissue in the atrium, cf U.S. Pat. No. 4,154,247. The cable is thus preshaped into a curve, loop or the like so a ring electrode on the cable makes contact with the atrial wall. This preshaping of the cable, however, makes implantation more difficult, and the contact with the atrial wall is unreliable.

Studies have shown that it would be advantageous with pacemakers providing ventricular stimulation to stimulate high up in tile ventricle, e.g. high up in the septum or occasionally, for practical reasons, in the superior part of the outer ventricular wall. Stimulation in the apex has proved to be capable of rapidly resolving acute problems, but some excess mortality has been observed in patients receiving this type of stimulation compared to stimulation in the upper atrial wall. Stimulation high up in the septum has been found to be similar to natural stimulation, since depolarization then comes through the septum and subsequently spreads across the ventricle with more efficient heartbeats as a result.

SUMMARY OF THE INVENTION

An object of the present invention is to eliminate the shortcomings of the above-described, known techniques and to achieve an electrode system making possible stimulation high up in the ventricle with both single and dual chamber pacemakers providing ventricular stimulation.

The above object is achieved in accordance with the principles of the present invention in an electrode system for pacemakers having at least one ventricular electrode having an exposed conductor portion capable of penetrating heart tissue, for screwing into or puncturing the part of the atrial wall facing the septum during implantation, and having a length so that it proceeds into the., septum or superior part of the outer ventricular wall. The tissue-penetrating portion of the electrode can be in the form of a helix, screw or needle. With a structure according to the invention, an electrode system is achieved with which the ventricular electrode is introduced into the septum or the superior part of the outer ventricular wall, i.e. the ventricular electrode will sense and excite tissue high up in the ventricle.

In an embodiment of the electrode system according to the invention, especially devised for DDD pacemakers, the system includes an atrial electrode, intended for placement in contact with heart tissue inside the atrium for sensing electrical activity and stimulation, and connected to a conductor for transmitting signals to and from the electrode, the conductors for the electrodes being arranged in a single cable. From the site of the atrial electrode, the conductor extends to the ventricular electrode, the atrial electrode being positioned in the lower part of the atrium when the ventricular electrode has been applied high up in the ventricle in this manner, a substantially "linear" electrode system is achieved which facilitates implantation, and the atrial electrode is in contact with heart tissue in the lower part of the atrium for sensing electrical activity and stimulation in the atrium, the ventricular electrode being implanted high up in the ventricle.

According to further embodiments of the electrode system according to the invention, the ventricular electrode is formed by a non-insulated terminal part of the otherwise insulated tissue-penetrating conductor which protrudes from the middle of a cowl forming the atrial electrode. Upon implantation, the needle, helical or screw-shaped conductor pierces or is screwed into the septum down to excitable heart tissue, the cowl then pressing against the inside of the lower atrial wall. The cowl can be made of carbon, platinum or titanium nitride.

DESCRIPTION OF THE PREFERRED EMBODIMENTS

Figure 1:
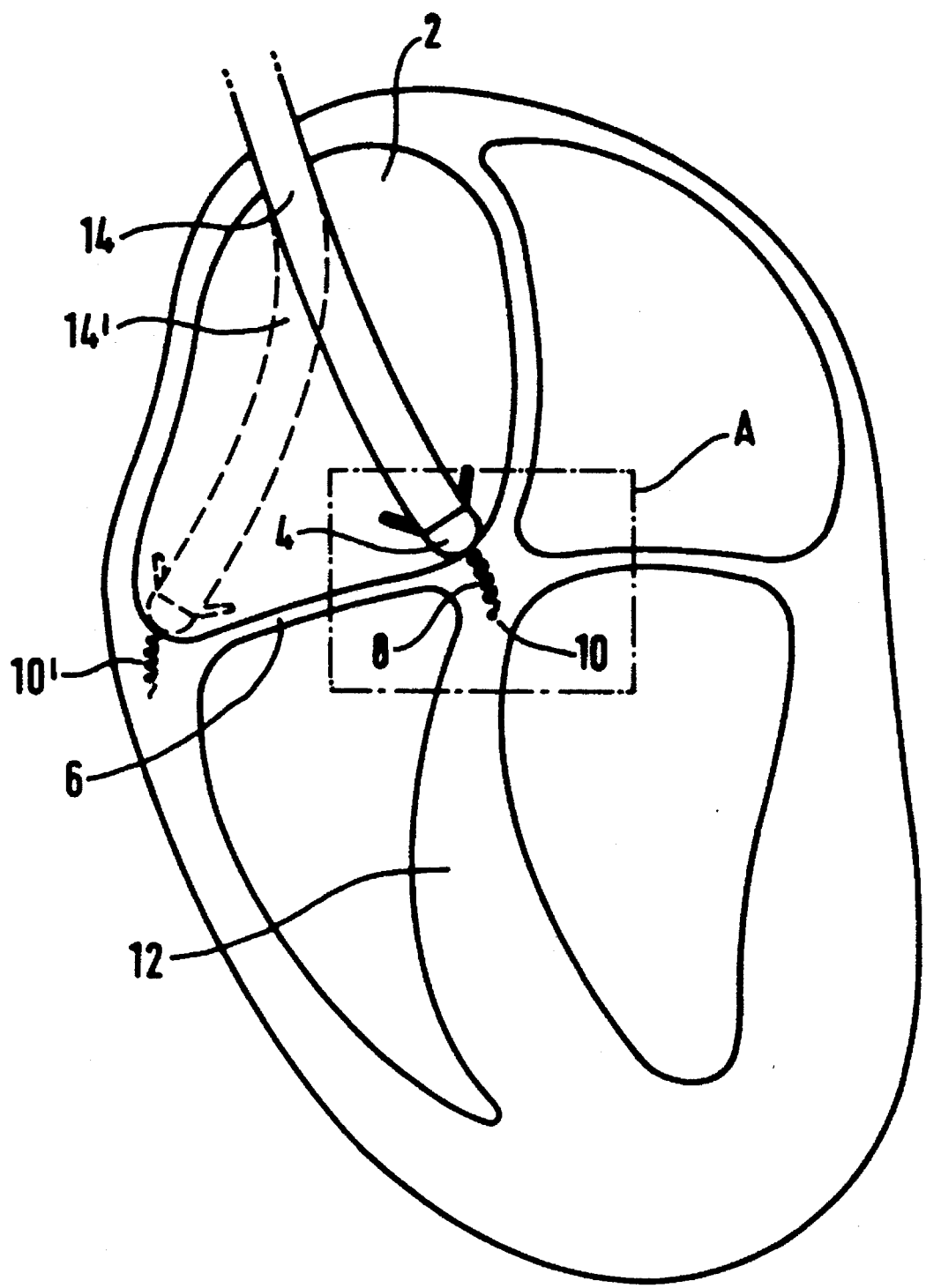
FIG. 1 is a schematic cross-section of a heart with an electrode system according to the invention implanted the vein.

FIG. 1 shows a schematic cross-section of a heart with the electrode system according to the invention introduced into the right atrium 2.

The electrode system includes an atrial electrode in the form of a cowl 4 made of carbon, platinum or titanium nitride which, in an implanted electrode system, presses against the inside of the lower part of the wall of the atrium 2, to one side of the heart valve 6. The atrial electrode can thus be used both for sensing electrical activity in and stimulating the atrium.

From the middle of the cowl 4 an insulated, tissue-penetrating conductor 8 protrudes formed by a conductor wire 8a covered by insulation 8b. The tissue-penetrating conductor 8 may, for example, be helical or screwshaped. The terminal part 10 of the helical or screw-shaped conductor 8 has no insulation and forms the ventricular electrode. The tissue-penetrating conductor 8 is intended for penetration, such as by a screwing action, into the septum 12, and has a length sufficient to permit the terminal part 10 to reach excitable ventricular tissue. The electrode system is installed simply by rotating the electrode system around its longitudinal axis so the tissue-penetrating conductor 8 is screwed into the septum 12, so that it is anchored therein.

Figure 3:
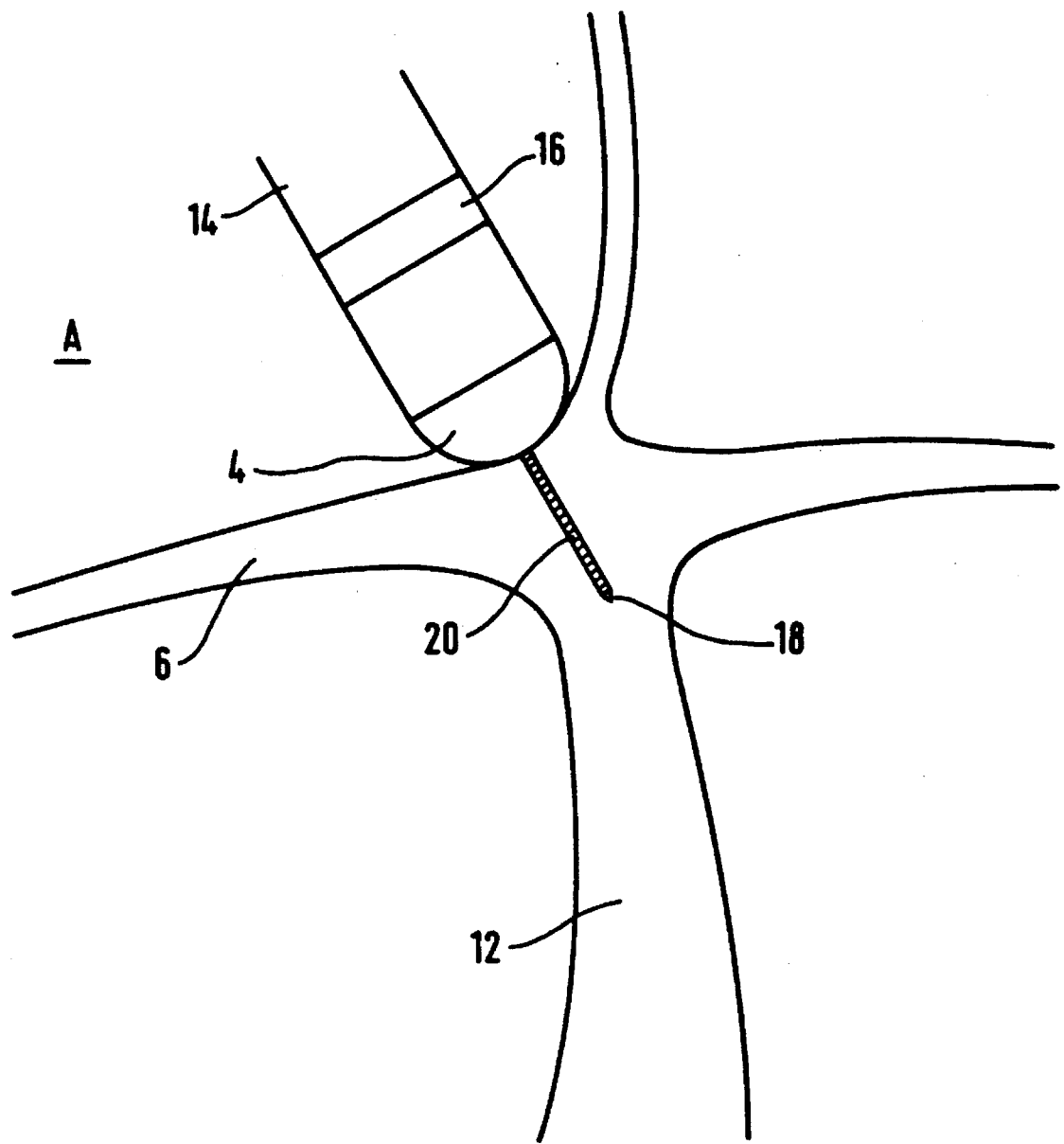

FIG. 3 shows an alternative version in which an insulated needle 20 protrudes from the middle of the cowl 4. The tip 18 of the needle 20 has no insulation and forms the ventricular electrode. When the electrode system is implanted, the needle 20 is pushed into the septum 12 so the tip 18 reaches excitable tissue.

The electrodes 10 and 18 thus are each electrically insulated from the electrode 4, and the ventricular electrode 10 or 18 senses electrical activity and stimulates tissue high up in the ventricle. As noted above, studies have shown that stimulation high up in the septum is more advantageous than stimulation in the apex since the former stimulation more closely resembles conditions in natural stimulation.

Alternately, the ventricular electrode 10 can be introduced into the superior part of the outer ventricular wall. For practical reasons, this version, shown with dashed lines in FIG. 1, could be preferable in certain situations.

Figure 2:
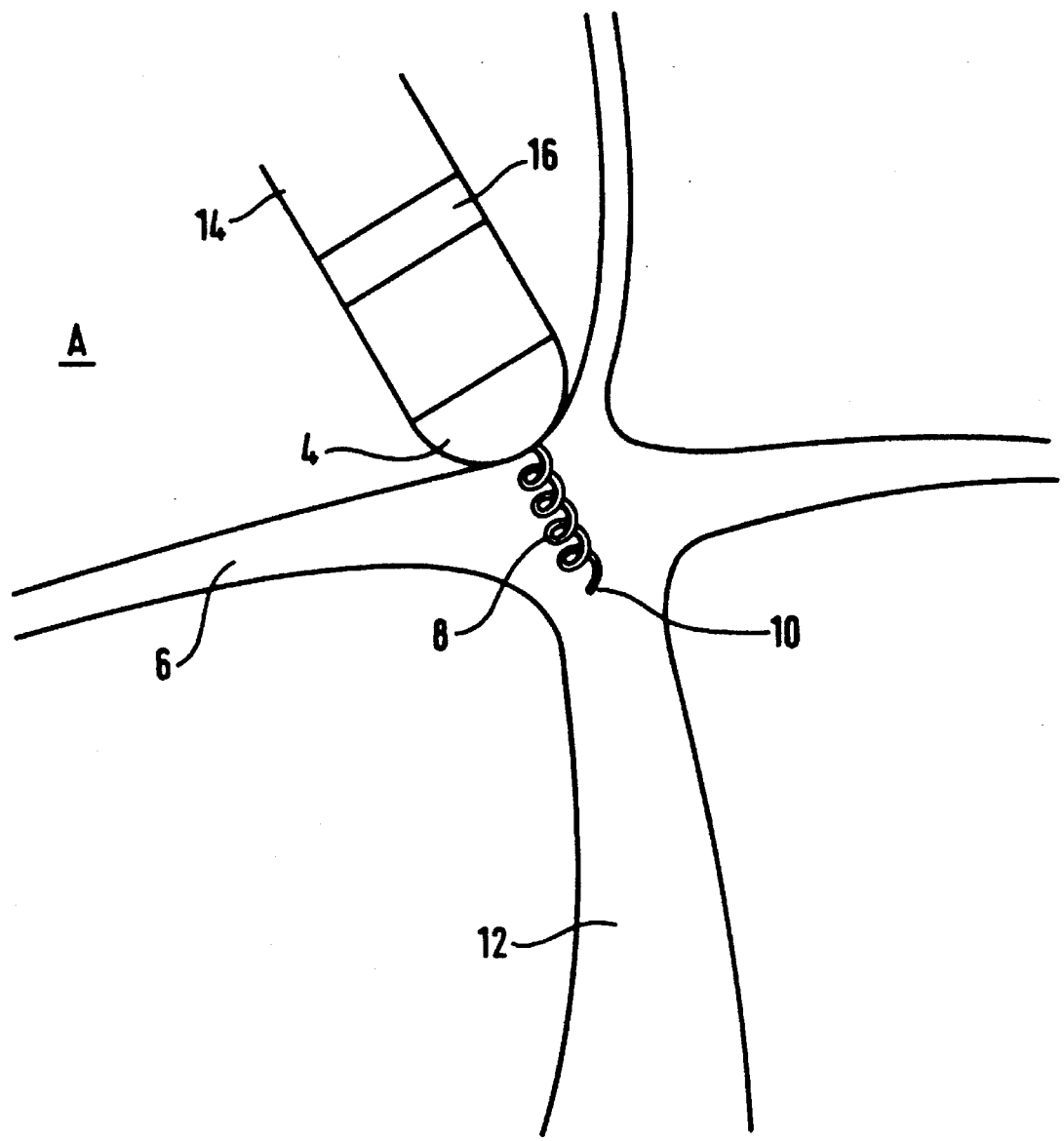
FIGS. 2 and 3 respectively show the central part A of FIG. 1, enlarged with two different versions of the ventricular part of the electrode system according to the invention.

As shown in FIG. 2, the wires (such as 8a) from the respecting electrodes 4, 10 or 18 for transmitting signals to and from the electrodes are arranged in a single cable 14 which runs to the pulse generator and sensing circuitry, such as an atrial sense and pace unit 22 and a ventricular sense and pace unit 23 in a pacemaker 21, which also contains other electronic equipment. Devising the electrode system with a single cable, even with DDD pacemakers, offers significant advantages, particularly during implantation, as noted above. The electrode system can then be easily introduced into the atrium through the vena cava. The same applies to the embodiment of FIG. 3.

The electrode system could also include an atrial indifferent electrode 16 in the form a metal ring arranged on the cable 14, cf. FIGS. 2 and 3.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode system for pacemakers, comprising:

ventricular electrode means for placement in contact with heart tissue in the ventricle for sensing electrical activity and for stimulating tissue, said ventricular electrode means including an insulated electrical conductor for transmitting signals to and from heat tissue;

said conductor terminating in an exposed, insulated tissue-penetrating terminal portion with an uninsulated tip insertable and anchorable in the atrial wall facing the septum, said terminal portion having a length proceeding into the region of the septum of superior part of the outer ventricular wall; and at least one atrial electrode means for placement in contact with heart tissue in the atrium for sensing electrical activity and stimulating tissue in the atrium, said atrial electrode means including a conductor for transmitting signals to and from tissue in the atrium, said conductor for said atrial electrode means and said conductor for said ventricular electrode means being disposed in a single cable having a cable end with said terminal portion of said ventricular electrode projecting from said electrode cable, and said atrial electrode means including an exposed electrode disposed at said cable end, said exposed electrode of said atrial electrode means and said terminal portion of said conductor of said ventricular electrode means being disposed relative to each other for causing said cable end and said exposed electrode of said atrial electrode means to be positioned in a lower part of the atrium when said terminal portion of said ventricular electrode means is disposed high up in the ventricle.

2. An electrode systems as claimed in claim 1 wherein said terminal portion of said conductor comprises a helix.

3. An electrode system as claimed in claim 1 wherein said terminal portion of said conductor comprises a screw.

4. An electrode system as claimed in claim 1 wherein said terminal portion of said conductor comprises a needle.

5. An electrode system as claimed in claim 1 wherein said exposed electrode of said atrial electrode means comprises an electrically conductive cowl disposed at said cable end.

6. An electrode system as claimed in claim 5 wherein said terminal portion of said conductor of said ventricular electrode means protrudes through said cowl.

7. An electrode system as claimed in claim 5 wherein said cowl consists of material selected from the group consisting of carbon, platinum and titanium nitride.

8. A method for stimulating a heart comprising the steps of:

introducing a ventricular electrode into an atrium of a heart, said ventricular electrode including an electrical conductor terminating in an exposed, tissue-penetrating portion;

inserting said exposed, tissue-penetrating portion into the atrial wall facing the septum to a depth proceeding into the region of the septum or superior part of the outer ventricular wall; and sensing electrical activity and stimulating tissue in the ventricle using said ventricular electrode.

9. A method for stimulating a heart as claimed in claim 8 comprising the additional steps of:

placing an atrial electrode in contact with heart tissue in the atrium of said heart; and sensing electrical activity and stimulating tissue in the atrium using said atrial electrode.

10. A method for stimulating a heart as claimed in claim 9 wherein said atrial electrode includes a conductor, and said method comprising the additional step of disposing said conductor or said ventricular electrode and said conductor of said atrial electrode in a single cable.

11. A method for pacing a heart as claimed in claim 10 wherein said atrial electrode terminates in a exposed electrode, and comprising the additional step of orienting said tissue-penetrating portion of said ventricular electrode and said exposed portion of said atrial electrode relative to each other for causing said exposed portion of said atrial electrode to be positioned in a lower part of the atrium when said exposed portion of said ventricular electrode is disposed high up in the ventricle of said heart.

12. An electrode system for pacemakers, comprising:

an insulated lead body having an end; and an insulated ventricular conductor and an atrial conductor extending through said lead body, said atrial conductor being electrically connected to an atrial electrode disposed at said end of said lead body and said insulated ventricular conductor extending through said atrial electrode and having a terminal portion projecting a distance beyond said end, said distance comprising a length which positions said terminal portion in the region of the septum or the superior part of the ventricular wall of a heart when said atrial electrode is adjacent the atrial wall of said heart, said terminal portion having an uninsulated tip.

13. A system for pacing a heart, comprising:

ventricular means for sensing ventricular activity and pacing a ventricle of a heart, including a ventricular electrode with a tip;

atrial means for sensing atrial activity in and pacing an atrium of said heart, including an atrial electrode; and a lead body connected to said ventricular means and said atrial means and on which said atrial electrode and said ventricular electrode are disposed exposed to said heart with said atrial electrode disposed at an end of said lead body and said tip of said ventricular electrode disposed a distance beyond said end, said lead body comprising means for positioning said atrial electrode and said tip of said ventricular electrode for respectively sensing activity in and pacing said atrium and said ventricle with said lead body disposed exclusively in said atrium.

* * * * *